US006544512B1

(12) United States Patent
White, Jr.

(10) Patent No.: US 6,544,512 B1
(45) Date of Patent: Apr. 8, 2003

(54) *PHOMA GLOMERATA* ATCC MYA-2373 FOR BIOCONTROL OF FUNGAL DISEASES IN PLANTS

(75) Inventor: James F. White, Jr., South River, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/517,790

(22) Filed: Mar. 2, 2000

Related U.S. Application Data

(60) Provisional application No. 60/123,099, filed on Mar. 5, 1999.

(51) Int. Cl.[7] .......................... A01N 63/00; C12N 1/00; C12N 1/20

(52) U.S. Cl. ...................... 424/93.5; 424/934; 424/405; 435/261; 435/254.1; 435/267; 435/911

(58) Field of Search .............................. 424/93.4, 93.5, 424/405; 435/254.1, 261, 267, 911, 262.5

(56) References Cited

U.S. PATENT DOCUMENTS

| | | | | | |
|---|---|---|---|---|---|
| 5,288,488 | A | * | 2/1994 | Backman et al. | 424/93 |
| 5,432,147 | A | * | 7/1995 | Winston et al. | 504/101 |
| 5,856,002 | A | * | 1/1999 | Mori | 528/334 |
| 5,985,795 | A | * | 11/1999 | Suganuma | 504/121 |

OTHER PUBLICATIONS

Arie et al., Control of soilborne clubroot disease of cruciferous plants by epoxydon from *Phoma glomerata* 1998, Plant Pathol. 47, No. 6, pp. 743–748 Abstract only.*

Brighton Crop Protection Conference—Pests and Diseases, vol. 3. British Crop Protection Council, Franham, U.K.

Desai, U. J. and P. K. Pfaffle, "Single–Step Purification of a Thermostable DNA Polymerase Expressed in *Escherichia coli*", 1995, *Biotechniques*, 19:780–784.

Galper, S., A. Sztejnberg, and N. Lisker," Scanning electron microscopy of the ontogeny of Ampelomyces quisqualis pycnidia", 1985, *Can. J. Microbiol.*, 31: 961–964.

Hasegawa et al., "Dating of the Human–Ape Splitting by a molecular Clock of Mitochondrial DNA", 1985, *J. Mol. Evol.*, 22:160–174.

Hutchinson et al., "*Phoma etheridgei* sp. nov. from black galls and cankers of trembling aspen (*Populus tremuloides*) and its potential role as a bioprotectant against the aspen decay pathogen *Phellinus tremulae*", 1994, *Can. J. Bot.*, 72: 1424–1431.

M. A. Innis, D. H. Gelfand, J. J. Sninsky and T. J. White (ed.), PCR protocols: A Guide to Methods and Applications, Academic Press, Inc. San Diego, CA.

Kiss, L. and Nakasone, K. K., "Ribosomal DNA internal transcribed spacer sequences do not support the species status of *Ampelomyces quisqualis*, a hyperparasite of powdery mildew fungi", 1998, *Current Genetics* 33: 362–367.

Morgan–Jones, G., 1967, *Phoma glomerata, CMI Desc. Pathol. Fungi Bact.*, No. 134; Commonwealth Mycological Institute.

Ouimet et al., "Environmental and nutritional factors affecting the in vitro inhibition of the vegetative growth of Venturia inaequalis by five antagonistic fungi", 1997, *Can. J. Bot.* 75: 632–639.

Sutton, B. C., 1980, *The Coelomycetes*, Commonwealth Mycological Institute, Kew, U.K.

White, J. F., Jr. and Morgan–Jones, G., "Studies in the Genus Phoma. VII. Concerning *Phoma glomerata*", 1987, Studies in the genus Phoma. VII. concerning *Phoma glomerata, Mycotaxon*, 28: 437–445.

* cited by examiner

*Primary Examiner*—David M. Naff
*Assistant Examiner*—Deborah K. Ware
(74) *Attorney, Agent, or Firm*—Licata & Tyrrell P.C.

(57) ABSTRACT

A biocontrol agent containing *Phoma glomerata* for suppressing development of fungal diseases on plants and methods of using this biocontrol agent in the suppression of fungal disease on plants are provided. The *Phoma glomerata* is preferably *Phoma glomerata* ATCC MYA-2373 that suppresses powdery mildew on plants.

2 Claims, No Drawings

*PHOMA GLOMERATA* ATCC MYA-2373 FOR BIOCONTROL OF FUNGAL DISEASES IN PLANTS

This application claims benefit of priority from Provisional Application Serial No. 60/123,099 filed Mar. 5, 1999.

BACKGROUND OF THE INVENTION

Currently a single strain of fungus, identified as *Ampelomyces quisqualis*, AQ10 Biofungicide, is in commercial use for biocontrol of powdery mildew on grapes and other crops (Hofstein, R. and B. Fridlender, 1994, Development of production, formulation and delivery systems, p. 1273–1280. In Brighton Crop Protection Conference-Pests and Diseases, vol. 3. British Crop Protection Council, Farnham, U.K.). The market for this biofungicide was over $1 million in 1998 and is expected to grow. Phylogenetically this strain is grouped within the divergent *Ampelomyces lade.*

A few reports have also identified Phoma species that are antagonistic to fungal plant pathogens. A Phoma sp (P66A) significantly reduced conidial germination of apple scab (*Venturia inequalis*) (Ouimet et al., 1997, *Can. J. Bot.* 75: 632–639) and *Phoma etheridgei* produced antifungal compounds inhibitory to the tree pathogen *Phellinus tremulae* (Hutchinson et al., 1994, *Can. J. Bot.*, 72: 1424–1431).

Several isolates of fungi, previously attributed to *genus Ampelomyces*, have now been shown to belong to genus Phoma through study of morphology and rDNA ITS1 sequence analysis. The species identified as *Phoma glomerata* has now been demonstrated to effectively colonize and suppress development of powdery mildew.

SUMMARY OF THE INVENTION

An object of the present invention is to provide a biocontrol agent which comprises *Phoma glomerata* for suppression of the development of fungal diseases such as powdery mildew on plants.

Another object of the present invention is to provide a method of suppressing development of fungal diseases such as powdery mildew on plants which comprises applying *Phoma glomerata* to a plant.

DETAILED DESCRIPTION OF THE INVENTION

Cultures isolated from several different genera of powdery mildews in both Europe and the United States have now been identified as *P. glomerata.*

These fungi are demonstrated herein to have a number of characteristics which render them readily distinguishable from Ampelomyces.

For example, stipitate pycnidia that develop into slow-growing colonies characterize *A. quisqualis* (Galper, S., A. Sztejnberg, and N. Lisker, 1985, *Can. J. Microbiol.*, 31: 961–964; and Kiss, L. and Nakasone,: K. K., 1998, *Current Genetics* 33: 362–367). Sessile pycnidia that develop into rapidly-growing colonies characterize *Phoma glomerata* (Boerema et al., 1965, *Persoonia*, 4: 47–68.; and White, J. F., Jr. and Morgan-Jones, G., 1987, *Mycotaxon*, 28: 437–445). For cultural growth rates, an average of 8±1 mm/day for the *P. glomerata* isolates was measured while an average of 0.8±0.1 mm/day for the Ampelomyces isolates were measured.

The process of pycnidia formation in association with the powdery mildew is also different between the two genera. Ampelomyces infects conidiogenous cells of the powdery mildew, internally colonizing them and forming pycnidia within the conidiophore so that the pycnidia appear stipitate. Phoma does not appear to internally-infect conidiogenous cells and pycnidia are formed directly on the leaf surface so that they are sessile. While many species of Phoma are known to be plant pathogens (Sutton, B. C., :1980, The Coelomycetes, Commonwealth Mycological Institute, Kew, U. K.), *P. glomerata* is not known to be a pathogen of plants. However, it is adept at saprophytic growth in tissues of plants and is known to be a secondary invader of diseased tissues, perhaps feeding on fungal saprophytes or pathogens of diseased tissues (Morgan-Jones, G., 1967, *Phoma glomerata, CMI Desc. Pathol. Fungi Bact.*, No. 134; Commonwealth Mycological Institute; Sutton, B. C., 1980, The Coelomycetes, Commonwealth Mycological Institute, Kew, U.K.; and White, J. F., Jr. and Morgan-Jones, G., 1987, Studies in the genus Phoma. VII. Concerning *Phoma glomerata*, Mycotaxon, 28: 437–445).

Dictyochlmydospores was observed in only *A. humuli* and the South River *P. glomerata*. However, the similarity of colonies and pycnidia of fungi identified as *A. heraclei, A. humuli* and *A. quercinus*, and the very, close sequence homology among these isolates suggests that all are isolates of *P. glomerata* that have been misidentified as species of Ampelomyces.

Further, phylogenetic analysis revealed considerable divergence in the sequences included in the Ampelomyces lade as compared to those of the *Didymella/Phoma* clade. Internal transcribed spacer region 1, also referred to herein as ITS1 sequences, of the South River *P. glomerata* (GenBank AF126816; SEQ ID NO:1) isolate and *A. heraclei* (ATCC 36804) were identical, while *P. glomerata* differed from *A. humuli* (GenBank AF035779; SEQ ID NO:5) in a single indel change. Because of their near identity with *P. glomerata*, both *A. heraclei* and *A. humuli* were excluded from the maximum likelihood analysis. *A. quercinus* differed in three changes: an indel and two nucleotide substitutions. Maximum likelihood analysis produced two nearly identical trees (tree length=204, consistency index=0.784, rescaled consistency index=0.608, homoplasy index=0.216, retention index=0.776). Thus, South River *P. glomerata* and *A. quercinus* are grouped together in the *Didymella/Phoma* lade, while the ITS1 sequence of putative South River *Ampelomyces quisqualis* isolate grouped in the Ampelomyces lade demonstrated close similarity to *Ampelomyces quisqualis* (ATCC 200245) isolated from grapes.

*P. glomerata* was demonstrated to be an effective biocontrol agent for suppressing development of fungal diseases such as powdery mildew on plants. In inoculation experiments, examination of inoculation sites after 30 days revealed that control leaves showed development of the powdery mildew cleistothecia while all leaves treated with *P. glomerata* conidia showed development of abundant pycnidia and suppression of powdery mildew cleistothecia in the white mycelium in and around the inoculation sites. Pycnidia were removed from leaves using fine needles and plated onto PDA+3. Colonies that developed were confirmed by observation of dictyochlamydospores, pycnidia and by subsequent sequence analysis to be *P. glomerata.*

The very slow growth in culture media, internal colonization of powdery mildews, and. apparent limitation to powdery mildew as a substrate, are all indicative that Ampelomyces are obligate parasites of powdery mildews. In contrast, the rapid growth of *P. glomerata* in culture and its known occurrence on many types of substrates are indicative that it is a facultative parasite of powdery mildew, infecting powdery mildew when it is available. Thus, from the widespread occurrence of this hyperparasite, it is believed that *P. glomerata* has untapped potential as a biocontrol agent. Further, with its rapid development in culture and its broader potential to grow on various substrates, it is believed that of *P. glomerata* is even more useful than species of Ampelomyces as biocontrol agents of fungal diseases, and in particular powdery mildew, of plants.

Accordingly, *P. glomerata* can be incorporated into a biocontrol agent for suppression of fungal diseases on plants. In a preferred embodiment, this biocontrol agent is used to suppress the development of powdery mildew plants. This biocontrol agent can be applied to plants, preferably on the leaves of plants, to suppress the development of fungal disease such as powdery mildew on the plant.

The following nonlimiting examples are provided to further illustrate the present invention.

EXAMPLES

Example 1

Isolation and Growth

Leaves of sycamore (*Platanus occidentalis*) bearing infections of powdery mildew (*Microsphaera penicillata*) were located in South River, N.J. in July of 1998. Leaves were examined microscopically and found to bear two types of pycnidia, including stipitate pycnidia typical of *A. quisqualis* and sessile pycnidia typical of species in genus Phoma. Both types of pycnidia were removed from leaves using fine needles and placed on PDA+3 [potato dextrose agar (Difco, Inc.) containing antibiotics gentamicin (40 mg/L), streptomycin (40 mg/L), and penicillin (20 mg/L)]. Two different fungi were consistently recovered. The stipitate pycnidia developed into slow-growing colonies whose characteristics corresponded to those expected for *A. quisqualis*. The sessile pycnidia developed into rapidly-growing colonies whose characteristics corresponded to those of *Phoma glomerata*.

With age, cultures of *P. glomerata* produced alternarioid dictyochlamydospores measuring 41+7.5×12+1.4 μm. To demonstrate that dictyochlamydospores belonged to *P. glomerata* rather than a species of Alternaria, several dictyochlamydospores were removed from colonies and placed onto fresh media. These dictyochlamydospores developed into colonies of *P. glomerata* with both pycnidia and dictyochlamydospores.

Agar plugs (6 mm in diameter) of mycelia cut from the margins of rapidly growing colonies of both the South River Ampelomyces and South River *P. glomerata* isolates were transferred onto five plates each of PDA+3 and incubated at room temperature for three weeks to measure growth rates.

Example 2

Koch's Postulates

A suspension of *P. glomerata* conidia from cultures grown on PDA+3 was produced using sterile water at a concentration of approximately $8\times10^6$ conidia/ml. The conidial suspension was used to inoculate *epiphyllous mycelia* of the powdery mildew *Phyllactinia guttata* on intact (left on the tree) leaves of oak (*Quercus coccinea*) by moistening an approximately 15 $mm^2$ region on the upper surface of leaves. Controls were set up by repeating the process using sterile water. Ten replicates of both the treatment and control were made and the sites of inoculation marked by placing white tape on the reverse of leaves at inoculation sites. The leaves were monitored for 30 days. To fulfill Koch's postulates, pycnidia were then removed from treated leaves and plated on PDA+3 medium to recover *P. glomerata*.

Example 3

Phylogenetic Analysis

To further confirm the identity of the mycoparasite as a species of Phoma and evaluate the extent to which isolates identified as Ampelomyces may instead belong to genus Phoma, DNA sequence analysis of the nuclear ribosomal DNA internal transcribed spacer region (ITS) from *P. glomerata*, several Ampelomyces spp., several Phoma spp., and other related species in genera Phaeosphaeria and Leptosphaeria was conducted. The South River *P. glomerata* and *A. quisqualis*, as well as ATCC cultures of *Ampelomyces heraclei* (ATCC 36804) and *A. quisqualis* (ATCC 200245) were grown on PDA+3. Fresh mycelia was ground in liquid nitrogen and genomic DNA was extracted using EASY-DNA™ Kit Protocol#3 in accordance with the manufacturer's's instructions. One μl of undiluted genomic DNA was amplified in a 50 μl reaction using the ITS primers ITS4 and ITS5 (White et al. 1990. Amplification and direct sequencing of fungal ribosomal RNA genes for phylogenetics. In M. A. Innis, D. H. Gelfand, J. J. Sninsky and T. J. White (ed.), PCR protocols: A Guide to Methods and Applications, Academic Press, Inc. San Diego, Calif.). Each reaction contained 10 mM Tris-HCl (pH 8.3), 50 mM KCl, 2.5 mM $MgCl_2$, 12.5 pmoles each dNTP, 25 pmole of each primer, and 2 U Taq polymerase (Desai, U. J. and P. K. Pfaffle, 1995, Biotechniques, 19:780–784). PCR (30 cycles) was carried out in a GeneAmp 9600 thermocycler (Perkin Elmer Corp., Foster City, Calif.) set to 95° C. for 10 seconds, 56° C. for 30 seconds and 72° C. for 2 minutes. Initial denaturation was conducted at 95° C. for 1 minute with a final extension for 10 minutes at 72° C. Successful PCR products, a single band (approximately 600 bp) on a 1% agarose gel, were precipitated in ethanol and dissolved in 50 μl of 10 mM Tris-HCl (pH 8). AMPLITAQ FS cycle sequencing reactions (Perkin Elmer Corporation, Foster City, Calif.) were prepared according to the manufacturer's protocol using 100 ng template and analyzed on an ABI 373A DNA Sequencer. Several additional ITS1 sequences identified as Ampelomyces, including *A. humuli*, and *A. quercinus*, along with Didymella (teleomorphs) and Phoma (anamorphs) were obtained from GenBank. Sequences of two other species of the Pleosporales, *Phaeosphaeria avenaria* and *Leptosphaeria microscopica* were included in the analysis as outgroups to aid in the evaluation of relationships. Alignments and analysis were accomplished using the SeqLab interface for the Wisconsin Package Version 9.1, including PAUP Portable version 4.0.0d55 for Unix (Genetics Computer Group (GCG), Madison, Wis.). Final alignment adjustments were made manually. Heuristic searches using maximum likelihood criteria were performed using the Hasegawa-Kishino-Yano model (Hasegawa et al., 1985, *J. Mol. Evol.*, 22:160–174). Bootstrapping involved 400 replicates.

Example 4

GenBank Accession Numbers

Gene sequences described herein are disclosed in GenBank under accession nos. AF126816 (SEQ ID NO:1), AF126817 (SEQ ID NO:2), AF126818 (SEQ ID NO:3) and AF126819: (SEQ ID NO:4).

What is claimed is:

1. A biocontrol agent for suppressing development of powdery mildew on plants, said biocontrol agent comprising a biologically pure culture of *Phoma glomerata* ATCC MYA-2373.

2. A method of suppressing development of powdery mildew on plants comprising contacting plants with an isolated *Phoma glomerata* ATCC MYA-2373.

* * * * *

SEQUENCE LISTING

<160> NUMBER OF SEQ ID NOS: 5

<210> SEQ ID NO 1
<211> LENGTH: 515
<212> TYPE: DNA
<213> ORGANISM: Phomo glomerata

<400> SEQUENCE: 1
aagtcgtaac aaggtttccg taggtgaacc tgcggaagga tcattaccta gagttgtagg 60
ctttgcctgc tatctcttac ccatgtcttt taagtacctt cgtttcctcg gcgggttcgc 120
ccgccgattg gacaatttaa accatttgca gttgcaatca gcgtctgaaa aaaacttaat 180
agttacaact ttcaacaacg gatctcttgg ttctggcatc gatgaagaac gcagcgaaat 240
gcgataagta gtgtgaattg cagaattcag tgaatcatcg aatctttgaa cgcacattgc 300
gccccttggt attccatggg gcatgcctgt tcgagcgtca tttgtacctt caagctctgc 360
ttggtgttgg gtgtttgtct cgcctctgcg tgtagactcg cctcaaaaca attggcagcc 420
ggcgtattga tttcggagcg cagtacatct cgcgctttgc actcataacg acgacgtcca 480
aaagtacatt tttacactct tgacctcgga tcagg 515

<210> SEQ ID NO 2
<211> LENGTH: 516
<212> TYPE: DNA
<213> ORGANISM: Ampelomyces quisqualis

<400> SEQUENCE: 2
gcagaaggat cattatcttc agtactttgc tactgacagg tgggcctrtt agcctgtata 60
gtattactac tgatgagcag catggccaca gcccttaccc ttgtcttttg tgcacctatg 120
tttctatagc aggctgacaa ccttgctgga cgaccctata ccatgaatat gttatcagcg 180
tctgaaaaac ctaaaattta caactttcaa caacagatct cttggttctg gcatcgatga 240
agaacgcagc gaaatgcgat aagtagtgtg aattgcagaa ttcagtgaat catcgaatct 300
ttgaacgcac attgcgcccc ttggtattcc atggggcatg cctgttcgag cgtcatttgt 360
acctcaagct atgcttggtg ttrggtgcct gtccctgttc tttcttggac tcaccttaaa 420
gcaattggca gccagtgttt tggtatagaa ctgcagcaca ttttgcaatt ctagtaccaa 480
agactggaac cagtaagacc ctctactcgt gacctc 516

<210> SEQ ID NO 3
<211> LENGTH: 570
<212> TYPE: DNA
<213> ORGANISM: Ampelomyces quisqualis

<400> SEQUENCE: 3
tttggaagta aaagtcgtaa caaggtttcc gtaggtgaac ctgcggaagg atcattatat 60
tcagtacttt gctactgtta gctgggcctg ttagtctgta tagtgttact actgatgagc 120
agcatggcca cggcccttac ccctgtcttt tgtgcaccta tgtttccgta gcgggttgac 180
aaccttgctg gacaacacca taacatgaat cttttatcag cgtctgaaaa aaacaaaatt 240
tacaactttc aacaacggat ctcttggttc tggcatcgat gaagaacgca gcgaaatgcg 300
ataagtagtg tgaattgcag aattcagtga atcatcgaat ctttgaacgc acattgcgcc 360
ccttggtatt ccatggggca tgtctgttcg agcgtcattt gtacctcaag ctatgcttgg 420
tgttgggtgc ctgtccttgt tctctcttgg actcacctta aagcaattgg cagccagtgt 480

-continued

```
tttggtatag aactgcagca cattttgcaa ttctagtgcc aaagactggg tccagtaaga    540

cttctactct tgactcgaat cagataggat                                     570


<210> SEQ ID NO 4
<211> LENGTH: 523
<212> TYPE: DNA
<213> ORGANISM: Phomo glomerata

<400> SEQUENCE: 4

ggaagtaaaa gtcgtaacaa ggtttccgta ggtgaacctg cggaaggatc attacctaga     60

gttgtaggct ttgcctgcta tctcttaccc atgtctttta agtaccttcg tttcctcggc    120

gggttcgccc gccgattgga caatttaaac catttgcagt tgcaatcagc gtctgaaaaa    180

acttaatagt tacaactttc aacaacggat ctcttggttc tggcatcgat gaagaacgca    240

gcgaaatgcg ataagtagtg tgaattgcag aattcagtga atcatcgaat ctttgaacgc    300

acattgcgcc ccttggtatt ccatggggca tgcctgttcg agcgtcattt gtaccttcaa    360

gctctgcttg gtgttgggtg tttgtctcgc ctctgcgtgt agactcgcct caaaacaatt    420

ggcagccggc gtattgattt cggagcgcag tacatctcgc gctttgcact cataacgacg    480

acgtccaaaa gtacattttt acactcttga cctcggatca ggt                      523


<210> SEQ ID NO 5
<211> LENGTH: 536
<212> TYPE: DNA
<213> ORGANISM: Ampelomyces humuli

<400> SEQUENCE: 5

tccgtaggtg aacctgcgga aggatcatta cctagagttg taggctttgc ctgctatctc     60

ttacccatgt cttttaagta ccttcgtttc ctcggcgggt tcgcccgccg attggacaat    120

ttaaaccatt tgcagttgca atcagcgtct gaaaaaactt aatagttaca actttcaaca    180

acggatctct tggttctggc atcgatgaag aacgcagcga aatgcgataa gtagtgtgaa    240

ttgcagaatt cagtgaatca tcgaatcttt gaacgcacat tgcgcccctt ggtattccat    300

ggggcatgcc tgttcgagcg tcatttgtac cttcaagctc tgcttggtgt tgggtgtttg    360

tctcgcctct gcgtgtagac tcgcctcaaa acaattggca gccggcgtat tgatttcgga    420

gcgcagtaca tctcgcgctt tgcactcata acgacgacgt ccaaaagtac atttttacac    480

tcttgacctc ggatcaggta gggatacccg ctgaacttaa gcatatcaat aagcgg        536
```